United States Patent
Frach et al.

(10) Patent No.: US 9,423,511 B2
(45) Date of Patent: Aug. 23, 2016

(54) VIRTUAL PET DETECTOR AND QUASI-PIXELATED READOUT SCHEME FOR PET

(75) Inventors: Thomas Frach, Aachen (DE); Andreas Thon, Aachen (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1924 days.

(21) Appl. No.: 12/600,072

(22) PCT Filed: Apr. 29, 2008

(86) PCT No.: PCT/IB2008/051663
§ 371 (c)(1),
(2), (4) Date: Nov. 13, 2009

(87) PCT Pub. No.: WO2008/142590
PCT Pub. Date: Nov. 27, 2008

(65) Prior Publication Data
US 2010/0219345 A1    Sep. 2, 2010

Related U.S. Application Data (60) Provisional application No. 60/938,282, filed on May 16, 2007.

(51) Int. Cl.
*G01T 1/20* (2006.01)
*G01T 1/164* (2006.01)
*A61B 6/03* (2006.01)

(52) U.S. Cl.
CPC ........... *G01T 1/1642* (2013.01); *G01T 1/1644* (2013.01); *A61B 6/037* (2013.01)

(58) Field of Classification Search
USPC ....................................................... 250/362
See application file for complete search history.

(56) References Cited

U.S. PATENT DOCUMENTS 4,864,140 A * 9/1989 Rogers et al. ................ 250/369
5,715,292 A * 2/1998 Sayag et al. .................. 378/98.8
(Continued)

FOREIGN PATENT DOCUMENTS

WO        2006111883 A2     10/2006
WO    WO 2008023451 A1 *    2/2008

OTHER PUBLICATIONS

Hagiwara et al. Three-dimensional image reconstruction for jPET-D4 using suitable histogramming method to DOI detector, 2004 IEEE Nuclear Science Symposium Conference Record, vol. 6 (Oct. 2004), pp. 3822-3825.*

(Continued)

*Primary Examiner* — David Porta
*Assistant Examiner* — Shun Lee (57) ABSTRACT

When designing detector arrays for diagnostic imaging devices, such as PET or SPECT devices, a virtual detector, or pixel, combines scintillator crystals (10, 20, 40) with photodetectors (12) in ratios that deviate from the conventional 1:1 ratio. For instance, multiple photodetectors can be glued to a single crystal to create a virtual pixel (10, 20, 40) which can be software-based or hardware-based. Light energy and time stamp information for a gamma ray hit on the crystal can be calculated using a virtualizer processor or using a trigger line network and time-to-digital converter logic. Additionally or alternatively, multiple crystals (54) can be associated with each of a plurality of photodetectors (52). A gamma ray hit on a specific crystal is then determined by a table lookup of adjacent photodetectors (52) that register equal light intensities, and the crystal (54) common to such photodetectors (52) is identified as the location of the hit.

16 Claims, 7 Drawing Sheets

(56) References Cited

U.S. PATENT DOCUMENTS

| | | |
|---|---|---|
| 6,114,703 A | 9/2000 | Levin et al. |
| 6,806,473 B2 | 10/2004 | Honda et al. |
| 7,164,136 B2 | 1/2007 | Aykac et al. |
| 7,166,848 B2 | 1/2007 | El-Hanany et al. |
| 7,173,251 B2 | 2/2007 | Fraser et al. |
| 2003/0223532 A1 | 12/2003 | Clinthorne et al. |
| 2004/0022538 A1 | 2/2004 | Shushakov et al. |
| 2005/0098732 A1 | 5/2005 | Liu et al. |
| 2006/0131508 A1 | 6/2006 | Burr et al. |
| 2008/0203309 A1 | 8/2008 | Frach et al. |

OTHER PUBLICATIONS

3 High Energy Position Imaging, Shengzu Chen, Introduction of foreign medical technology and equipment, vol. 4, No. 3, pp. 6-11, Jun. 1998.

* cited by examiner

VIRTUAL PET DETECTOR AND QUASI-PIXELATED READOUT SCHEME FOR PET

CROSS REFERENCE TO RELATED APPLICATIONS

This application claims the benefit of U.S. provisional application Ser. No. 60/938,282 filed May 16, 2007, which is incorporated herein by reference.

The present application finds particular utility in positron emission tomography (PET) and/or single photon emission computed tomography (SPECT) scanners in medical applications using pixels of different sizes or the like. However, it will be appreciated that the described technique(s) may also find application in other types of scanning systems and/or other medical applications.

Scintillator pixel size in PET is a primary factor determining the spatial resolution of the resulting image. Thus, depending on the application in mind, the scanner geometry and pixel size are optimized to maximize the scanner performance and competitiveness. For instance, typical pixel size used in a full-body scanner is 4×4 $mm^2$, while in a brain or an animal scanner a pixel size of 2×2 $mm^2$ to 1×1 $mm^2$ may be used to increase the resolution. A 1:1 coupling between scintillator pixels and photo-detectors is often used to optimize performance, and translates into a need for a custom-designed light detector for each specific application. This, however, implies significant changes to the light detection chain as well. In conventional systems using photomultiplier tubes and Anger logic, this further means that the light guide design and the size of the photomultiplier tubes must be adapted, thus leading to higher system development and manufacturing costs.

Having a larger number of detectors coupled with each scintillator element improves spatial resolution, and the plurality of detectors can determine where in the scintillator the scintillation event occurs. However, timing resolution for determining time-of-flight measurements can be compromised, since each of the multiple detectors only sees a fraction of the light and may receive it with different delays. By contrast, coupling each scintillator with a corresponding detector optimizes the timing resolution, but reduces spatial resolution. The single detector that receives all of the light from the crystal can provide an accurate time stamp, but resolution is limited to the size of the scintillator.

Additionally, in conventional crystal-based PET systems, the scintillator crystals are coupled to the light detectors either on 1:1 basis (pixelated readout) or through a light guide using Anger logic for crystal identification. A drawback of pixelated readout is the vast number of channels and, as the crystal size gets smaller, the cost of the photodetectors. Anger logic-based systems, on the other hand, map many crystals onto few photodetectors, leading to smaller number of channels at the cost of increased pile-up and dead time and thus reduced count rate capability.

Thus, there is an unmet need in the art for systems and methods that facilitate overcoming the deficiencies noted above.

In accordance with one aspect, a virtual pixel array for a diagnostic imaging system includes a virtual pixel comprising at least a scintillator crystal, a plurality of photodetectors optically coupled to the scintillator crystal, which generate output signals in response to scintillations in the crystal, and a virtualizer that processes the output signals associated with a gamma ray hit on the scintillator crystal as detected by the plurality of photodetectors and calculates a time stamp for the gamma ray hit.

In accordance with another aspect, a method of method of calculating a time stamp for a virtual pixel includes receiving a gamma ray hit on a scintillator crystal of the virtual pixel, evaluating output signals from each of a plurality of photodetectors optically coupled to the scintillator crystal to determine an energy and a photodetector time stamp for each photodetector associated with the gamma ray hit, and calculating a total energy of the gamma ray hit by combining the energies detected by the plurality of photodetectors associated with the gamma ray hit. The method further includes calculating a time stamp for the gamma ray hit as a function of the photodetector time stamp registered by at least one photodetector in the plurality of photodetectors.

Yet another aspect relates to a detector array for a diagnostic imaging device, including a plurality of photodetectors arranged in an array, and a plurality of scintillator crystals arranged in an array and optically coupled to the plurality of photodetectors, wherein the photodetector array and the scintillator array being offset from each other such that some of the scintillator crystals are coupled to a different number of photodetectors than other scintillator crystals. The detector array further includes a processor that identifies a scintillator crystal that has been hit by a gamma ray based on an output signal generated by one or more of the plurality of photodetectors optically coupled to the scintillator crystal hit by the gamma ray.

One advantage is that detector array design cost is reduced.

Another advantage resides in a universal detector array chip for multiple sizes of scanners.

Another advantage resides in improved compatibility between detector arrays or scanners utilizing crystals of different sizes.

Still further advantages of the subject innovation will be appreciated by those of ordinary skill in the art upon reading and understand the following detailed description.

The innovation may take form in various components and arrangements of components, and in various steps and arrangements of steps. The drawings are only for purposes of illustrating various aspects and are not to be construed as limiting the invention.

Figure 1:
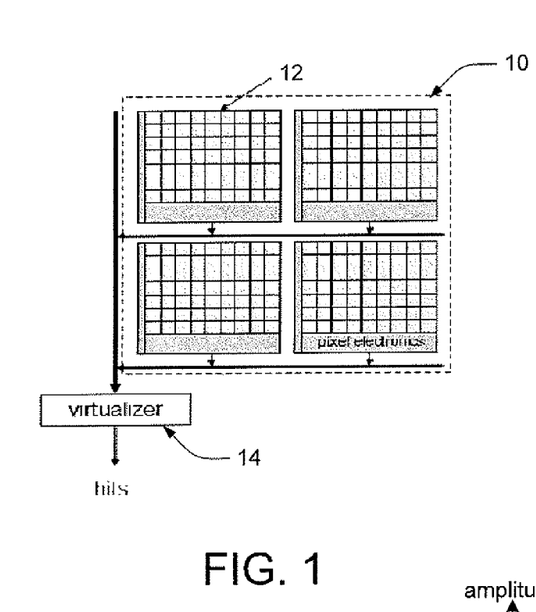
FIG. 1 illustrates a virtual pixel that is employed on a detector chip that is configured to be optically coupled with any of a variety of scintillator arrays.

FIG. 1 illustrates a virtual pixel that is employed on a detector chip that is configured to be optically coupled with any of a variety of scintillator arrays (not shown). A "virtual" pixel can be a configurable combination of photodetectors and scintillator crystals, designed to act or appear as a given standard type of detector, such as a 4×4 array of 1×1 mm$^2$ photodetectors, or some other size array of a given size of photodetectors. The universal chip reduces manufacturing costs by enabling the same chip to be used on a variety of PET scanners. Although the systems and methods described herein are presented largely with respect to PET systems, it will be appreciated that such systems and/or methods may be used in conjunction with SPECT systems, as well as other radiation detection systems.

The redesign, manufacturing and testing of a new CMOS-based photodetector is a costly endeavor. To overcome this impediment, it is desirable to design a digital silicon photomultiplier detector that is suited for all kinds of applications in PET and/or SPECT. This problem can be surmounted by combining several small pixels into larger virtual pixels, which can be performed either in hardware, or in software. For example, four solid state detectors can be arranged in a square and can be operated as four independent detectors, grouped together to operate as a single detector, etc. The virtual pixel facilitates introducing virtualization to PET detectors based on a digital silicon photomultiplier, which integrates the light sensing element and the readout circuits onto the chip. Thus, the virtual pixel illustrated in FIG. 1 shows a software-based virtualization scheme, and subsequent figures (showing hardware-based virtualization schemes) show additional circuits that facilitate connecting several smaller photodetectors 12 into larger virtual pixels, which are matched to the application without sacrificing detector performance. As a result, a one-size-fits-all detector is designed, thus saving costs on design and manufacturing and leading to improved readout performance compared to a monolithic pixel of the same size.

In one embodiment the virtual pixel comprises a scintillator crystal 10 of a given size and multiple smaller photodetector pixels 12. In accordance with various aspects, an algorithm is employed by a virtualizer 14 (e.g. a processor) to combine the partial detector data into a final "hit," which describes a perceived gamma ray registration event at a portion of the virtual pixel crystal. Additionally, hardware that improves timing resolution and reduces data rate may be employed in conjunction with the virtual pixel.

The following example is presented to illustrate a scenario in which the virtual pixels are useful. For instance, it may be desirable to implement a photodetector with a smallest practical pixel size, such as 1×1 mm$^2$ in the case of an animal scanner, and then glue larger crystals to 2×2 or 4×4 photodetectors, if the detector is to be used in a brain or a human scanner. To further this example, either 4 or 16 photodetector pixels can detect the photons emitted from the crystal and an external logic, implemented in a separate field programmable gate array (FPGA) or the like, can combine the pixels to get the energy and the time of the gamma hit. This, however, can lead to a reduced timing resolution, as the pixels see only ¼ or ¹⁄₁₆ of the light emitted by the crystal, which can be particularly damaging as large pixels are used in time-of-flight PET scanners where the timing information is particularly important. To build virtual pixels without compromising the timing resolution, the trigger lines of the photodetectors can be combined together in a symmetrical way, as described below with regard to FIG. 2.

According to other aspects, software may be employed to permit a user to select (e.g., via a pull-down menu or some other interface) virtual pixel size based on an application for which the virtual pixel is to be employed in a detector array. Software may also be employed to select active trigger lines in a hard virtual pixel, which facilitates manipulating behavior of the virtual pixel.

Figure 2:
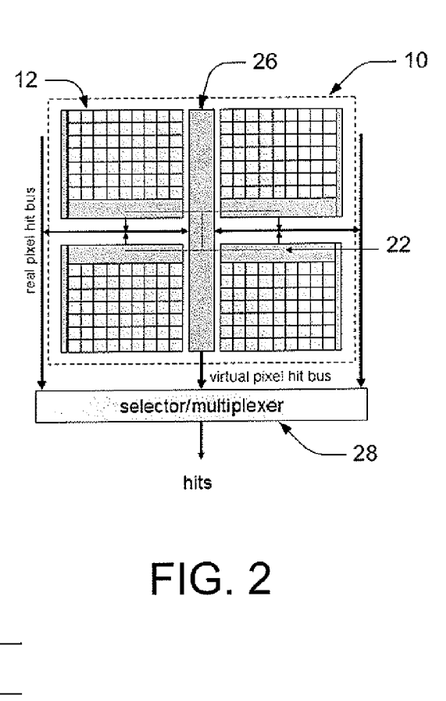
FIG. 2 shows a hardware-based virtual pixel that is employed on a universal chip in a manner similar to the software-based virtual pixel described above.

FIG. 2 shows a hardware-based virtual pixel that is employed on a universal chip in a manner similar to the software-based virtual pixel described above. The virtual pixel includes trigger lines 22 that connect smaller photodetectors 12 comprised by the virtual pixel. Additionally, time-to-digital converters (TDC) 26 can be employed to measure the time of the first photon arriving at any of the combined pixels. Moreover, a combination of the validation signal is employed to validate the resulting hit, as described in U.S. patent application Ser. No. 11/467,670, entitled "Digital Silicon Photomultiplier," filed on Aug. 28, 2006. The validation signal is used to determine if the event is a real hit or if the acquisition has been started by a dark count. It is used to discriminate real hits from noise, while the first trigger level that is used to stop the TDC is set just above the noise floor to get an optimal timing resolution. In the virtual pixel, a validation signal is useful because the first cell that fires stops the TDC and starts the acquisition. Therefore, in the case of a dark count, the validation prevents the pixel from executing a full acquisition and then discarding the data right afterwards. Doing so would increase the dead time of the pixel, as any hit during that time would lead to an incorrect time stamp and also likely to an incorrect energy.

The validation works in the following manner: in a digital silicon photomultiplier, a trigger network is hierarchically subdivided into vertical column lines that trigger a horizontal trigger line, which is then connected to the TDC. The validation of a hit means that more than one column trigger line indicates a hit for the hit to be validated. For instance, according to an example, if four columns exhibit activity within approximately 5 ns, then the event can be considered a real hit. Otherwise, the pixel can be quickly reset to get prepare for the next hit. The probability of detecting 4 dark counts in a respective line within 5 ns is sufficiently low to make the foregoing validation scheme highly efficient. Thus, to validate a hit in a virtual pixel, at least one of the photodetectors validates the hit. It will be appreciated that other numbers of columns exhibiting activity (e.g., more than four, less than four, etc.), as well as other time periods (e.g., more than 5 ns, less than 5 ns, etc.) may be employed in conjunction with the various validation schemes described herein, and that the foregoing example is illustrative in nature and not intended to limit the scope of the described aspects.

One difference between "soft" and "hard" virtualization is that in the hard virtualization case, the photodetectors 12 included in the virtual pixel contribute directly to the time stamp of the hit, as their trigger lines are connected through a balanced network connected to an additional TDC component 26. In some embodiments, the TDC component includes an accumulator as well, which sums partial photon counts from the respective photodetectors comprised by the virtual pixel. Thus, the photon statistics remain substantially unchanged. Although a 2×2 mm$^2$ virtual pixel is shown in FIG. 2, four of the virtual pixels can be used to implement a 4×4 mm² pixel, if desired, and so on. A selector/multiplexer 28 selects which data to forward to one or more output buffers (not shown). In one embodiment, software determines which trigger lines to activate in the hard virtual pixel in order to manipulate pixel behavior.

In soft virtualization, the time stamp and energy of the final hit are computed by an algorithm, which can also be implemented in an external FPGA for performance reasons, if desired. The algorithm uses the time stamps and energies from all pixels included in the virtual pixel, and computes the time stamp and the energy of the hit as if all pixels were connected together. While computing the total energy is straight-forward, computing the time stamp can be more complicated.

Figure 2A:
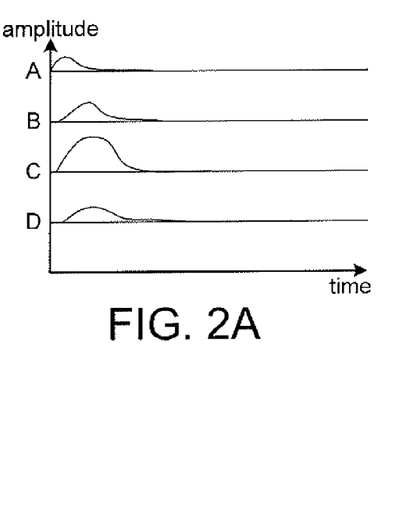
FIG. 2A illustrates output signals from four photodetectors, responsive to scintillation of a crystal with respective pulses A, B, C, and D.

Several ways of computing the time stamp of the combined hit are possible. For instance, the time stamp can be computed in a way similar to that which is used in Anger-logic, as an energy-weighted sum of the partial time-stamps. That is, as illustrated in FIG. 2A, each of the four illustrated detectors responds to the scintillation with a respective pulse A, B, C, and D, whose beginning is indicative of time and whose area is indicative of energy. However, this method involves several multiply-add operations and a fixed-point division to be implemented in hardware. Another method uses the time stamp of the hit with the highest energy (e.g., C, in the example of FIG. 2A), assuming this time stamp to be most accurate because of the photon statistics. Alternatively, the earliest time-stamp (e.g., A, in FIG. 2A) can be used independently of the energy of the partial hit—this method mimics the hard-wiring of the trigger lines of the virtual pixels. Although there are some sources of error (e.g., quantum noise, TDC shifts, and numerical errors) that may affect the time stamp more than in the hard virtualization case, soft virtualization is relatively cheap and does not need any additional hardware, which can lead to a potentially higher manufacturing yield because of a lower number of gates.

Figure 3:
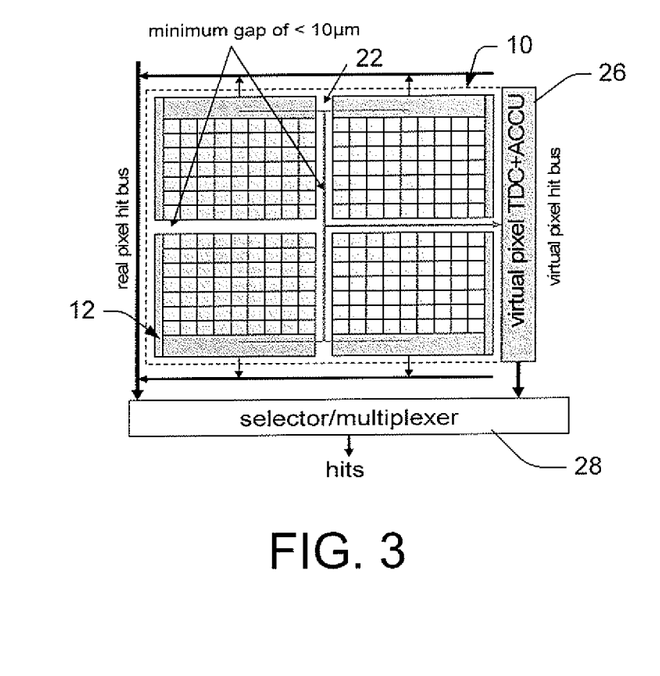
FIG. 3 is an illustration of a hardware-based virtual pixel that facilitates using Anger logic to determine a time stamp for a gamma ray hit on the virtual pixel.

FIG. 3 is an illustration of a hardware-based virtual pixel that facilitates using Anger logic to determine a time stamp for a gamma ray hit on the virtual pixel. For instance, a photodetector chip can be optimized for a scanner with 2×2 mm² crystals, as shown in the figure. The same chip can be used in a full-body scanner, where 2×2 pixels are combined to realize a 4×4 mm² virtual pixel with timing resolution optimized for time of flight (TOF). On the other hand, the same detector could also be connected to a light guide and 1×1 mm² crystals, for instance in an animal scanner. Alternatively, a mapping scheme can also be used without a light guide. The circuitry implementing the Anger logic can be placed on the chip itself, thus making the type of readout transparent to the rest of the system. The orientation of the photodetector pixels 12 comprised by the virtual pixel can be optimized to minimize any "dead area" due to the electronics, as shown in FIG. 3. Additionally, space between pixels 12 can be utilized for processing circuitry and the like.

To minimize the amount of circuitry used for the virtualization, some existing components can be re-used (e.g., TDC, I/O buffers, accumulators, etc). The trigger network 22 forms a symmetrical balanced tree of buffers. Additionally, hit validation logic (not shown) is connected in a similar way to facilitate separating triggers due to dark counts from the real hits. At least one of the validation signals from each pixel can indicate a valid hit for the acquisition to continue. The validation logic in the real pixels can be superseded by the validation logic of the virtual pixel in order to accomplish this. Moreover, the acquisition sequence can be controlled by a virtual pixel state machine.

Additionally, the readout time of the virtual pixel is substantially identical to the readout time of the small pixels making up the virtual pixel, compared to a monolithic large pixel where the readout time increases with pixel size. This is the result of the parallel readout of the smaller pixels, which can be done faster than in a large pixel having more lines to read.

It is to be understood that although various aspects described herein distinguish between software-based virtual pixels and hardware-based virtual pixels, a combination of both hard and soft virtual pixels is intended to fall within the scope and spirit of this application. For example, a combination of separate hard and soft virtual pixels can be employed in a single virtual pixel array. According to another example, a single virtual pixel can employ any or all of the features of a soft virtual pixel, such as described with regard to FIG. 1, as well as any or all of the features of a hard virtual pixel, such as described with regard to FIGS. 2 and 3. Moreover, a virtual pixel array, whether employing soft or hard virtual pixels, can employ virtual pixels of different sizes, in order to localize a desired pixel size on a given region of interest or the like.

In another embodiment, a combination of virtual pixel sizes is used in a single detector array. For instance, 1×1 virtual pixels can be employed about a region of interest to maximize spatial resolution at that location, while larger virtual pixels (e.g., 2×2, 4×4, etc.) may be employed elsewhere. According to yet another embodiment, a 1×1 virtual pixel is employed for spatial resolution purposes, and a 2×2 or 4×4 virtual pixel adjacent thereto is employed for timing resolution purposes. In this example, a pattern of alternating virtual pixel sizes is employed in the same detector array.

Figure 4:
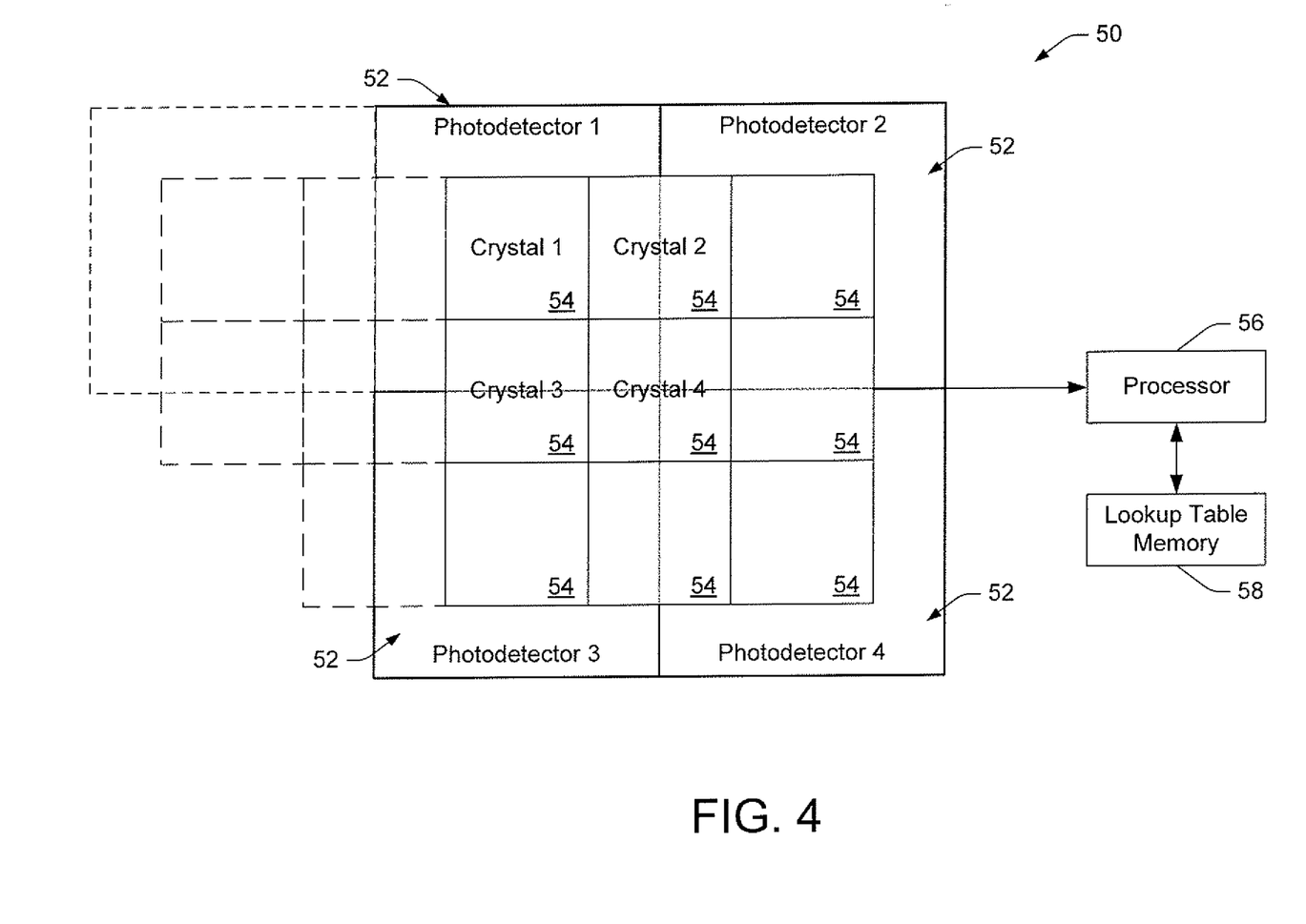
FIG. 4 illustrates an example of a quasi-pixelated readout scheme for PET imaging systems, maintaining the advantage of classical pixelated readout methods, including direct coupling of crystals to individual photodetectors, while reducing the number of readout channels by a factor of four.

FIG. 4 illustrates an example of a quasi-pixelated readout scheme for PET or SPECT imaging systems, maintaining the advantage of classical pixelated readout methods, including direct coupling of crystals to individual photodetectors, while reducing the number of readout channels by a factor of four. A detector array 50 is described, in which the number of photodetectors 52 and electronics channels used to achieve a given level of sensitivity is reduced, thus allowing reduction in the costs of the detector front-end. Additionally, direct coupling of the crystals 54 to the photosensitive surface mitigates a need for a light guide. Moreover, crystal pitch can be half the size of photodetector pitch. As shown in FIG. 4, crystals 54 are connected directly to the sensitive surface of the photodetectors 52. The crystal size is approximately ½ of the photodetector pitch, leading to a 4:1 mapping. The crystals are arranged such that one crystal delivers all light to the center photodetector alone, 2 crystals share the light 1:1 with the detectors adjacent to each side half, and 4 crystals share ¼ of the light with the detectors adjacent at the corners. A simple lookup table-based logic (e.g., discretized Anger logic or the like) can be used to identify the crystal by measuring the ratio of light shared between the neighboring photodetectors.

The detector array 50 offers the advantage of allowing pixelated readout with only ¼ of the channels needed in conventional designs, thus reducing the costs of the electronics backend. Contrary to true pixelated readout, only 25% of the gamma ray hits lead to single-channel dead time. 50% of the hits lead to double-channel dead time, and in the remaining 25% of the hits, four channels are dead due to the light sharing between neighboring photodetectors. The detector additionally allows for the detection of Compton crosstalk when individual interactions are separated by at least two crystals.

In order to combat X-ray fluorescence, which can lead to crystal misidentification, the observation of a 3×3 photodetector field can be used as an input to a more refined discretized lookup table. In FIG. 4, for example, crystal 1 delivers 100% of its received light to photodetector 1, crystals 2 and 3 each present 50% of their received light with photodetector pairs 1 and 2, and 1 and 3, respectively. Crystal 4 distributes its received light equally to all four photodetectors, and so on.

According to another example, the mounting of the crystals 54 in a staggered, offset position relative to the photodetectors 52 improves spatial resolution. For instance, if 100% of the light from a given crystal is received by only one of the photodetectors, then a processor 56 determines that the crystal is under the center of the photodetector registering the light. For example, the processor evaluates a lookup table stored in memory 58 to identify the specific crystal transferring light to the photodetector the position of which is known. In FIG. 4, when photodetector 1 registers a light transfer and no other photodetectors register a transference, the processor determines that the hit occurred on crystal 1, since crystal 1 is the only crystal that can transfer a full burst of light to photodetector 1.

If the amount of light received by two adjacent photodetectors is equal, then the processor similarly determines that the light is from the scintillation crystal that spans those two photodetectors. For instance, if photodetector 1 registers a transference of light, a lookup of the table in memory 58, performed by the processor 56, will indicate that the hit was received at crystal 1, crystal 2, or crystal 3. By evaluating whether other photodetectors registered an equal light transference, the processor can cross-index the photodetectors to isolate the precise crystal. In this example, if photodetector 2 registers a light transference equal to that registered by photodetector 1, then the processor determines that the hit occurred at crystal 2. Alternatively, if photodetector 3 registers a light burst equal to that registered by photodetector 1, then the processor determines that crystal 3 received the hit.

If the amount of the light received by four contiguous photodetectors is equal, then the scintillator crystal is determined to be positioned equally under the four detectors. In FIG. 4, if all four photodetectors register a substantially equal light transference, then the processor determines that the hit was received at crystal 4. In this manner, relatively simple ratios can be used to resolve the spatial position of the scintillation with a resolution smaller than the size of the detector.

It will be appreciated that good spatial resolution and good timing resolution are not mutually exclusive factors. For example, an embodiment can employ a pixel with one Geiger-mode avalanche photodiode (APD), which can facilitate achieving good timing resolution for any size scintillator crystal of a given aspect ratio.

Figure 5:
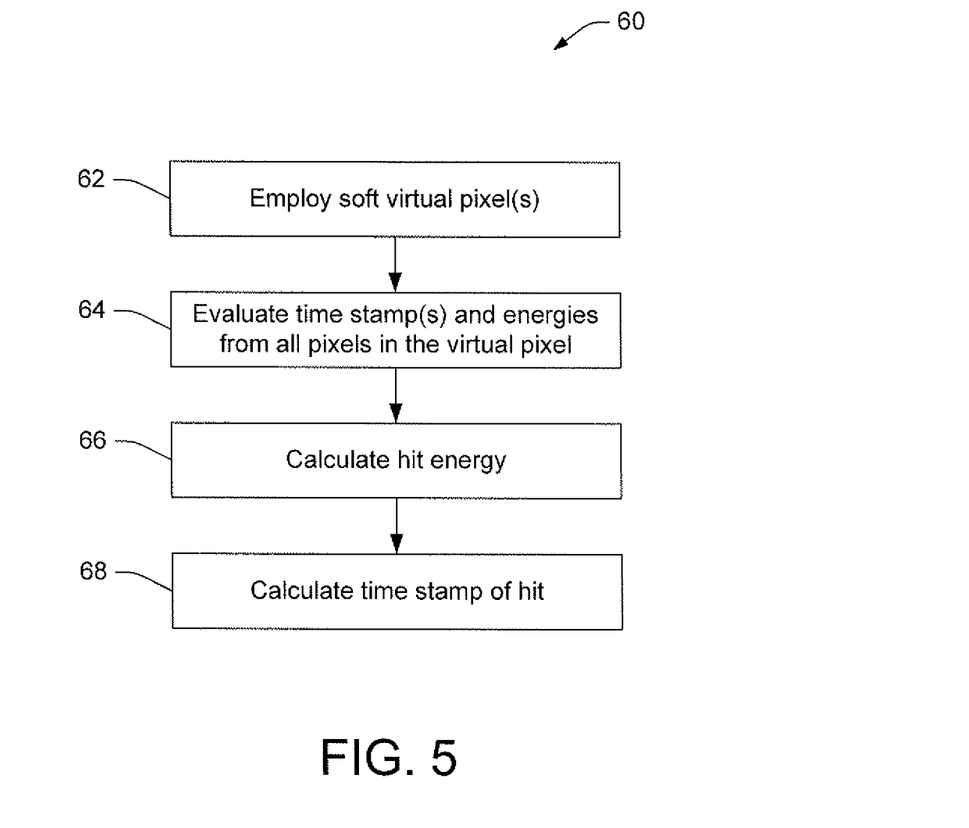
FIG. 5 illustrates a method of using a software-based virtual pixel to facilitate combining smaller real pixels.

FIG. 5 illustrates a method 60 of using a software-based virtual pixel to facilitate combining smaller real pixels. At 62, a software-based virtual pixel is employed, such as the virtual pixel described with regard to FIG. 1. At 64, the time stamps and energies from all real pixels in the virtual pixel are evaluated. Total energy is computed at 66, for instance by summing all energies registered on real pixels in the virtual pixel. Time stamp for the hit registered on the virtual pixel is computed, at 68. Computing the time stamp is performed according to one or more different techniques.

For instance, according to one embodiment, the time stamp is computed using an Anger logic technique, wherein the computed time stamp is the energy-weighted sum of the partial time stamps. According to another embodiment, the time stamp computed at 68 is the time stamp of the highest-energy hit, which is assumed to be the most accurate based on photon statistics. According to yet another embodiment, the time stamp computed at 68 is the earliest time stamp associated with the hit, independent of the energy of the partial hit. This embodiment mimics a hard-wired trigger line such as the trigger line described with regard to the hardware-based virtual pixel of FIGS. 2 and 3, as well as FIG. 6 below. In this manner, virtual pixel cost is minimized because the software-based virtual pixel does not need any additional hardware.

Figure 6:
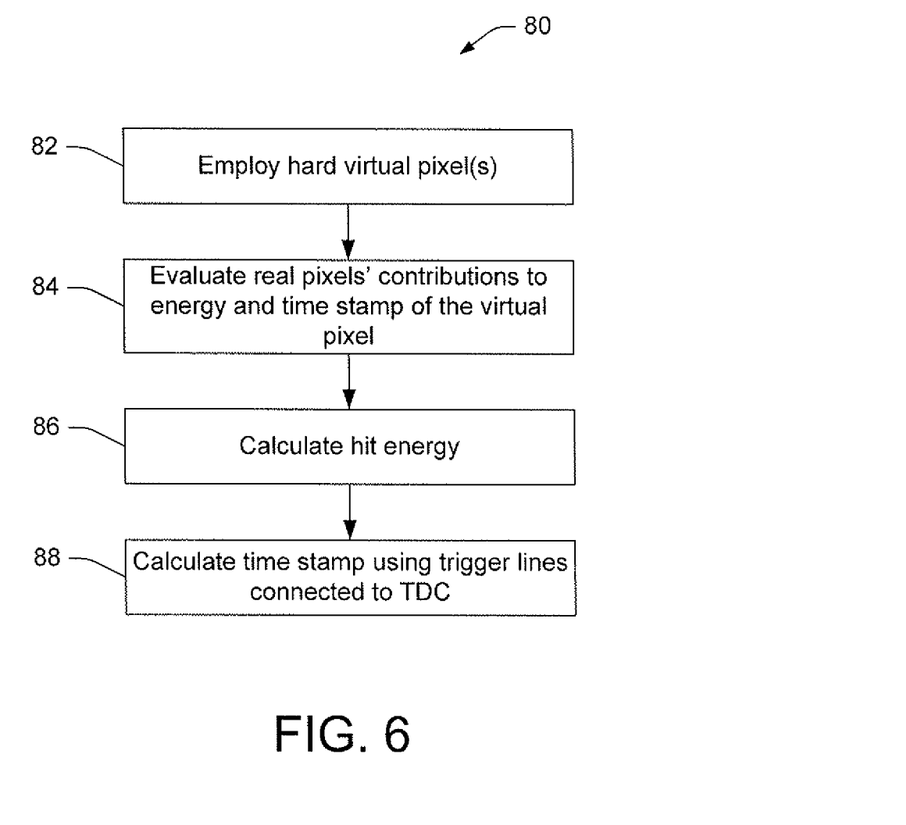
FIG. 6 illustrates a method of using a hardware-based virtual pixel to facilitate combining smaller real pixels.

FIG. 6 illustrates a method 80 of using a hardware-based virtual pixel to facilitate combining smaller real pixels. At 82, a hardware-based virtual pixel is employed, which comprises a plurality of smaller real pixels, such as is described with regard to FIGS. 2 and 3, above. At 84, contributions of each real pixel to total energy and time stamp of the virtual pixel are evaluated. At 86, the total energy registered at the virtual pixels is calculated, such as by summing the energies of all real pixels in the virtual pixel.

At 88, the time stamp for a gamma ray hit is determined using hardwired trigger lines and a TDC and component. For instance, since all pixels comprised by the hard virtual pixel have trigger lines connected through a balanced network connected to a TDC, all pixels can contribute directly to the time stamp of the hit.

According to another embodiment, Anger logic can be employed to facilitate using a standard chip with a given crystal size for larger or smaller scanning applications. For instance, a photodetector chip can be optimized for a scanner with 2×2 mm$^2$ crystals, and same chip can be used in a full-body scanner, if four 2×2 pixels are combined to realize a 4×4 mm$^2$ virtual pixel with timing resolution optimized for TOF. Additionally or alternatively, the same detector chip can be connected to a light guide and 1×1 mm$^2$ crystals, for example in an animal scanner. Still furthermore, the 2×2 mm$^2$ chip can be coupled to 1×1 mm$^2$ crystals in a mapping such as is described above with regard to FIG. 4. The circuitry implementing the Anger logic can be placed on the same chip, thus making the type of readout transparent to the rest of the system. The orientation of the photodetector pixels building a virtual pixel can be optimized to minimize the dead area due to the electronics, as shown in FIG. 3, above.

Figure 7:
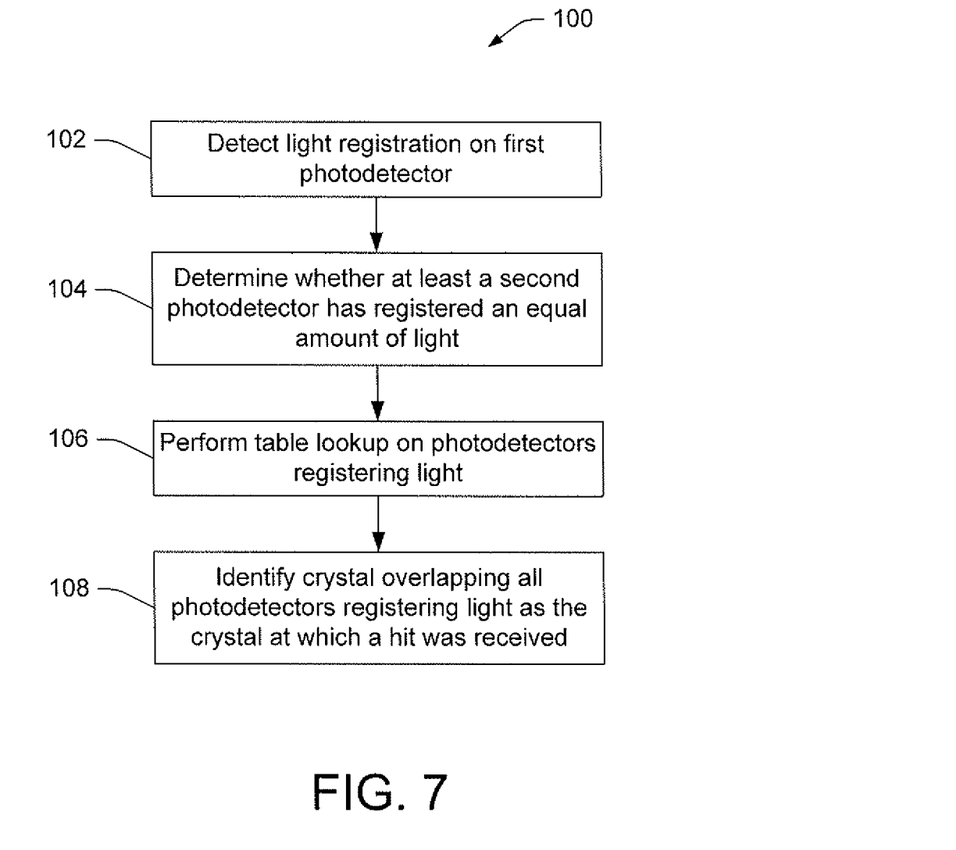
FIG. 7 illustrates a method of enabling a quasi-pixelated readout scheme and reducing readout channels for a detector comprising photodetectors directly coupled to a number of scintillation crystals.

FIG. 7 illustrates a method 100 of enabling a quasi-pixelated readout scheme and reducing readout channels for a detector comprising photodetectors directly coupled to a number of scintillation crystals, such as detector 50 described above. In this example, the crystals have a pitch one-half the size of the pitch of the photodetectors to which they are coupled. According to one embodiment, At 102, a hit is detected on a first photodetector. At 104, a determination is made regarding whether a second photodetector, adjacent to the first photo detector, has registered a hit comprising a substantially equal amount of light. At 106, a table lookup is performed for all adjacent photodetectors registering substantially equal hits, in order to determine where the hit was received. At 108, a crystal that received the hit is identified based on the photodetectors that registered the substantially equal hits.

According to an example, a first photodetector registers a hit at 102 and no second photodetector registers a hit per the determination at 104. In this scenario, a lookup of the table at 106 results in an identification of a single crystal at 108, which is the crystal that is coupled solely to the first photodetector and does not overlay any other photodetectors. According to another example, wherein two adjacent photodetectors receive hits of substantially equal magnitude as detected at 102 and 104, then the lookup at 106 will result in an identification, at 108, of the crystal that overlaps both of the photodetectors and no other photodetector. According to yet another example, four photodetectors register substantially equal hits as determined at 102 and 104. In this case, the lookup at 106 will identify the crystal that overlaps a corner of all four photodetectors, at 108.

Figure 8:
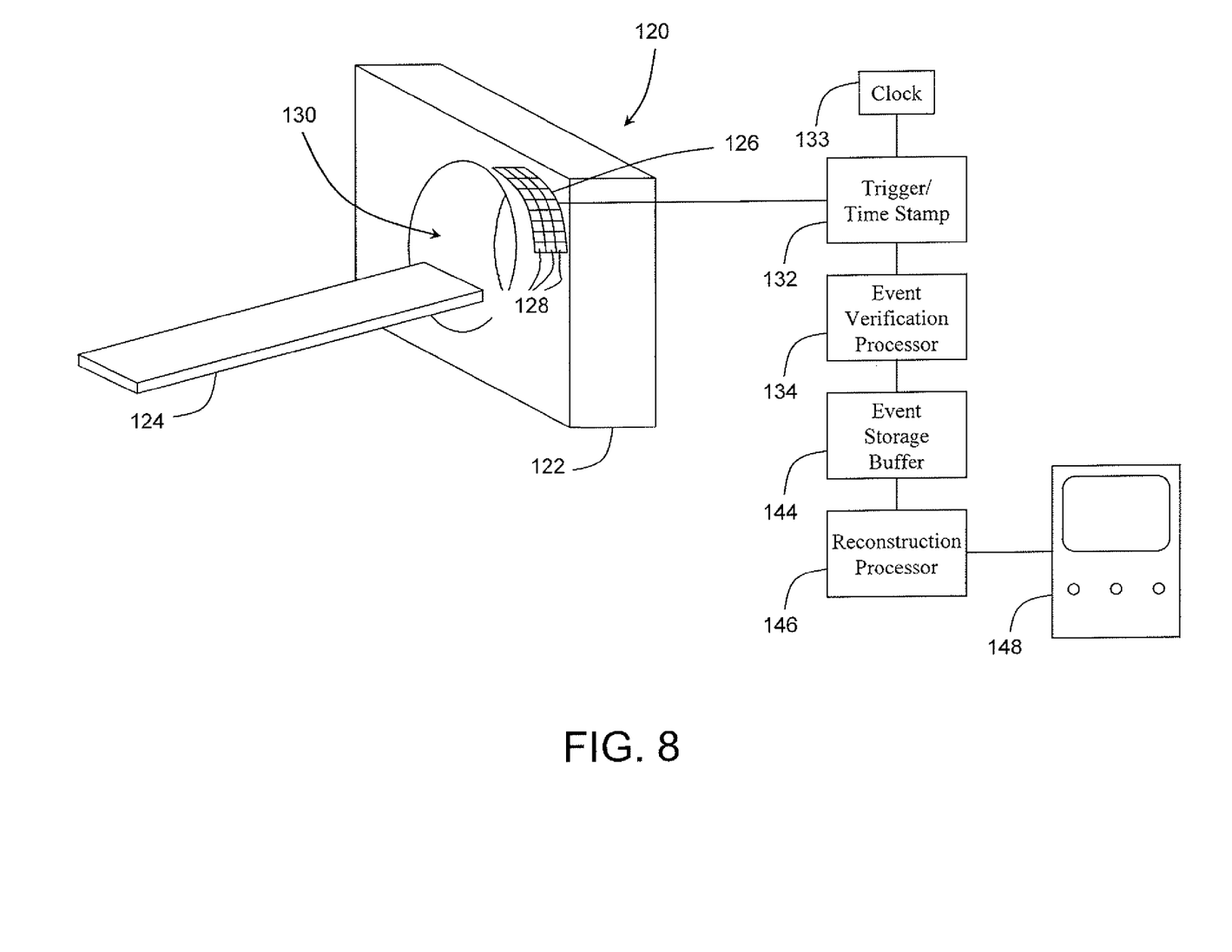
FIG. 8 illustrates a diagnostic imaging device such as may be employed in conjunction with one or more of the detectors, detector arrays, pixel arrays, virtual pixels, and/or methods described herein.

FIG. 8 illustrates a diagnostic imaging device 120 such as may be employed in conjunction with one or more of the detectors, detector arrays, pixel arrays, virtual pixels, and/or methods described herein. The diagnostic imaging device 120 includes a housing 122 and a subject support 124. Enclosed within the housing 122 is a detector array 126. The detector array 126 includes a plurality of individual detector elements 128. The array 126 is arranged so that detector elements 128 are distributed evenly about an imaging region 130. The detector array 126 can be a ring of detectors 128, multiple rings, or discrete flat panels disposed opposing each other. Whatever the actual placement or arrangement of the detectors 128, it is preferable to arrange the detectors such that each detector has a plurality of counterpart detectors across the imaging region to facilitate coincidence detection. In positron emission tomography (PET), pairs of gamma rays are produced by a positron annihilation event in the imaging region and travel in opposite directions. These gamma rays are detected as pairs, with a slight delay (on the order of nanoseconds) between detections if one gamma ray travels farther to reach a detector than the other.

Before the PET scan commences, a subject is injected with a radiopharmaceutical. The radiopharmaceutical contains a radioactive element coupled to a tag molecule. The tag molecule is associated with the region to be imaged, and tends to gather there through normal body processes. For example, rapidly multiplying cancer cells tend to expend abnormally high amounts of energy duplicating themselves. So, the radiopharmaceutical can be linked to a molecule, such as glucose that a cell typically metabolizes to create energy, gather in such regions and appear as "hot spots" in the image. Other techniques monitor tagged molecules flowing in the circulatory system.

For PET imaging the selected radioisotope emits positrons. The positron can only move a very short distance (on the order of nanometers) before it is annihilated in an annihilation reaction that creates two oppositely directed gamma rays. The pair of gamma rays travel in opposite directions at the speed of light striking an opposing pair of detectors.

When a gamma ray strikes the detector array 126, a time signal is generated from a leading edge of the resultant electrical pulse. A triggering processor 132 monitors each detector 128 for an energy spike, e.g., integrated area under the pulse, characteristic of the energy of each received gamma ray. The triggering processor 132 checks a clock 133 and stamps each detected gamma ray with a time of leading edge receipt stamp. The time stamp is first used by an event verification processor 134 to determine which gamma rays are a pair which defines a line of response (LOR). Because gamma rays travel at the speed of light, if detected gamma rays arrive more than several nanoseconds apart, they probably were not generated by the same annihilation event and are discarded. Timing is especially important in TOF-PET, as the minute difference in substantially simultaneous events can be used to further localize the annihilation event along the LOR. As computer processor clock speeds become faster, the higher the accuracy with which an event can be localized along its LOR. In a SPECT camera, the LOR or trajectory for each detected gamma ray is determined by collimation.

LORs are stored in an event storage buffer 144, and a reconstruction processor 146 reconstructs the LORs into an image representation of the subject using filtered backprojection or other appropriate reconstruction algorithm. The reconstruction can then be displayed for a user on a display device 148, printed, saved for later use, and the like.

Having thus described the preferred embodiments, the invention is now claimed to be:

1. A virtual pixel array for a diagnostic imaging system, including:
   a virtual pixel comprising at least a scintillator crystal and a plurality of photodetectors optically coupled to the scintillator crystal, which generate output signals in response to scintillations in the crystal, wherein the photodetectors are smaller than the crystal to which they are coupled; and
   a virtualizer that processes the output signals associated with a gamma ray hit on the scintillator crystal as detected by the plurality of photodetectors and calculates a time stamp for the gamma ray hit.

2. The system according to claim 1, wherein the virtual pixel is a software-based virtual pixel and the virtualizer employs an algorithm that calculates the time stamp.

3. The system according to claim 2, wherein the virtualizer calculates the time stamp as an energy-weighted sum of a partial photodetector time stamp from the output signals of each of the plurality of photodetectors.

4. The system according to claim 2, wherein the virtualizer calculates the time stamp as a function of the output signal of a photodetector registering a highest energy level relative to other photodetectors in the virtual pixel.

5. The system according to claim 2, wherein the virtualizer calculates the time stamp as a function of an earliest photodetector time stamp registered by a photodetector in the virtual pixel.

6. The system according to claim 1, wherein the virtual pixel is a hardware-based virtual pixel, and includes a network that connects a trigger line from each of the plurality of photodetectors to a time-to-digital converter.

7. The system according to claim 6, further including a selector/multiplexer that selects time stamp data from all photodetector time stamps received over the network for forwarding to at least one output buffer.

8. The system according to claim 1, wherein the virtual pixel array is disposed in a diagnostic imaging device and the virtualizer includes:
   a routine for evaluating energies and time stamps associated with a plurality of photodetectors in the virtual pixel in response to a gamma ray hit;
   a routine for calculating total energy associated with the gamma ray hit; and
   a routine for calculating a time stamp for the gamma ray hit.

9. The system according to claim 1, wherein the plurality of photodetectors includes 4 photodetectors arranged in a 2×2 array.

10. A method of calculating a time stamp for a virtual pixel, including:
   receiving a gamma ray hit on a scintillator crystal of the virtual pixel;

evaluating output signals from each of a plurality of photodetectors optically coupled to the scintillator crystal to determine an energy and a photodetector time stamp for each photodetector associated with the gamma ray hit, wherein the photodetectors are smaller than the scintillator crystal to which they are optically coupled;

calculating a total energy of the gamma ray hit by combining the energies detected by the plurality of photodetectors associated with the gamma ray hit; and calculating a time stamp for the gamma ray hit as a function of the photodetector time stamp registered by at least one photodetector in the plurality of photodetectors.

11. The method according to claim 10, further including calculating the time stamp for the gamma ray hit as an energy-weighted sum of a partial photodetector time stamp from each of the plurality of photodetectors associated with the gamma ray hit.

12. The method according to claim 10, further including calculating the time stamp as a function of a photodetector time stamp of a photodetector registering a highest energy level relative to other photodetectors in the virtual pixel.

13. The method according to claim 10, further including calculating the time stamp as a function of an earliest photodetector time stamp registered by a photodetector in the virtual pixel.

14. The method according to claim 10, further including calculating the time stamp as a function of partial time stamps received at a time-to-digital converter via a network connection a trigger line from each of the plurality of photodetectors.

15. A reconfigurable pixel array, including:
an array of photodetectors;
an array of scintillator crystals in which the crystals are any of a plurality of selectable sizes; and
a processor that processes the output signals associated with a gamma ray hit on one of the scintillator crystals as detected by a respective portion of the array of photodetectors to calculate a time stamp for the gamma ray hit;
wherein the photodetectors are smaller than the scintillation scintillator crystals to which they are attached.

16. The pixel array according to claim 15, wherein the array size is selectable.

* * * * *